United States Patent [19]

Friedlander

[11] Patent Number: 5,055,460
[45] Date of Patent: Oct. 8, 1991

[54] METHOD FOR WEIGHT LOSS

[76] Inventor: Mitchell Friedlander, 2460 Peachtree Rd., NW., Suite 1810, Atlanta, Ga. 30305

[21] Appl. No.: 514,744

[22] Filed: Apr. 26, 1990

[51] Int. Cl.$^5$ ............... A61K 31/62; A61K 31/60; A61K 31/52; A61K 31/135
[52] U.S. Cl. ................... 514/161; 514/165; 514/263; 514/653; 514/909; 514/910
[58] Field of Search ............... 514/165, 653, 909, 910 514/159, 263, 161

[56] References Cited

U.S. PATENT DOCUMENTS

| | | | |
|---|---|---|---|
| 2,801,951 | 8/1957 | Cooper | 514/165 |
| 3,080,287 | 3/1963 | Lewenstein | 514/165 |
| 4,716,042 | 12/1987 | Blank et al. | 514/165 |
| 4,880,791 | 11/1989 | Weithmann et al. | 514/161 |

OTHER PUBLICATIONS

Krieger et al., "Ephedrine, Caffeine and Aspirin Promote Weight Loss in Obese Subjects", Clinical Research, vol. 38, No. 2, 1990.
WLD Rev. Nutr. Diet., (1987), vol. 50, pp. 1–56, "Obesity: A Disorder of the Sympathetic Nervous System", A. G. Dulloo et al.
International Journal of Obesity, (1982), vol. 6, pp. 343–350, "Ephedrine, A Potential Slimming Drug, Directly Stimulates Thermogenesis . . . ", Bukowiecki et al.
International Journal of Obesity, (1981), vol. 5, pp. 183–187, "Ephedrine as an Anorectic: The Story of the 'Elsinore Pill'", A. Malchow-Moller, et al.
Br. J. Nutr., (1982), vol. 47, pp. 21–32, "A Study of the Thermic Responses to a Meal and to Sympathomimetic Drug (Ephedrine in Relation . . . ", J. Morgan et al.
Br. J. Nutr., (1984), vol. 52, pp. 179–196, "Thermogenic Drugs for the Treatment of Obesity: Sympathetic Stimulants in Animal Models", A. G. Dulloo et al.
The New England Journal of Medicine, (1984), vol. 311, pp. 1549–1558, "Thermogenesis in Brown Adipose Tissue as an Energy Buffer", Jean Himms-Hagen.
The Am. J. Of Clinical Nutr., (1985), vol. 42, pp. 83–94, "Enhanced Thermogenic Responsiveness During Chronic Ephedrine Treatment in Man", A. Astrup et al.
American Physiological Society, (1985), pp. E507–E515, "Contribution of Bat and Skeletal Muscle Thermogenesis Induced by Ephedrine in Man", A. Astrup et al.
The Am. J. of Clinical Nutr., (1986), vol. 43, pp. 388–394, "The Thermogenic Properties of Ephedrine/Methylxanthine Mixtures: Animal Studies", A. G. Dulloo et al.
International Journal of Obesity, (1986), vol. 10, pp. 467–481, "The Thermogenic Properties of Ephedrine/Methylxanthine Mixtures: Human Studies", A. Dulloo et al.
Am. J. Clin. Nutr., (1987), vol. 45, pp. 564–569, "Aspirin as a Promotor of Ephedrine-Induced Thermogenesis: Potential Use in the . . . ", A. G. Dulloo et al.
International Journal of Obesity, (1987), vol. 11, pp. 163–168, "Does Ephedrine Promote Weight Loss in Low-Energy-Adapted Obese Women?", P. Pasquali et al.
International Journal of Obesity, (1987), vol. 11, pp. 23–26, "Thermogenic Agents in the Treatment of Human Obesity: Preliminary Results", R. Pasquali et al.
Gen. Pharmac., (1987), vol. 18, pp. 559–561, "Anorectic Effect of Ephedrine", M. R. Zarrindast, et al.
International Journal of Obesity, (1989), vol. 13, 152, "The Therapeutic Dilemma of Ephedrine in Obesity and the Inefficacy of Caffeine", M. Cesari et al.

Primary Examiner—Frederick E. Waddell
Assistant Examiner—Kevin Weddington
Attorney, Agent, or Firm—Oblon, Spivak, McClelland, Maier & Neustadt

[57] ABSTRACT

A method for producing or maintaining weight loss by administering to a human a composition containing an effective amount of each of caffine, aspirin and ephedrine. The pharmaceutical composition can be administered concurrently with caloric restriction or in the absence of caloric restriction, for the purpose of reducing weight or maintaining body weight.

28 Claims, 2 Drawing Sheets

METHOD FOR WEIGHT LOSS

BACKGROUND OF THE INVENTION

1. Field of the Invention

The present invention relates to a composition which is useful for inducing weight loss in humans and to a treatment for obesity. More specifically, the invention is directed to a composition containing aspirin, caffeine and ephedrine and use of this composition for producing weight loss.

2. Description of the Background

Western society is increasingly concerned with personal weight and appearance. Diets and weight loss programs are extensively advertised and utilized by a large segment of Western society with varying degrees of effectiveness. There is a continuing search for new and effective means to facilitate weight loss.

Obesity, originally presumed to result from simple overeating or the combination of overeating with inactivity, has more recently been attributed to a genetic predisposition in combination with poor diet and exercise habits. It has been suggested that predisposition to obesity is associated with a defect in the sympathetic nervous system. This defect is manifested as a high efficiency in food utilization and a reduced thermogenic response to food intake. In normal persons, food intake results in a thermogenic response, that is, an increase in body temperature in which the caloric content of food is expended as heat. Some studies suggest that persons with a genetic predisposition to obesity are metabolically more efficient than lean persons, storing excess caloric energy as body fat. In obese persons, thermogenic defects may make a significant contribution to weight gain in the absence of controlled food intake. Calories not expended as heat are stored as excess weight. See Dulloo, A. G. and Miller, D. S., *Wld. Rev. Nutr. Diet.*, vol. 50, pp. 1-56, 1987.

Pharmaceutical compositions have been developed with the purpose of stimulating thermogenesis and thereby inducing weight loss. Ephedrine stimulates thermogenesis in laboratory animals, presumably by stimulating brown adipose tissue. In theory, catecholamines activate thermogenesis in brown adipose tissue in animals by binding adrenergic receptors (Buckowiecki, L., Jahjah, L., and Follea, N., *International Journal of Obesity*, vol. 6, pp. 343-350, 1982). Numerous studies have been published on the thermogenic response of humans and mammals to ephedrine treatment (See for example Morgan, J. B., York, D. A., Wasilewska, A. and Portman, J., *Br. J. Nutr.*, vol. 47, pp. 21-32, 1982; Dulloo, A. G. and Miller, D. S., *Br. J. Nutr.*, vol. 52, pp. 179-196, 1984; Himms-Hagen, J., *Seminars in Medicine of the Beth-Israel Hospital, Boston*, vol. 311, no. 24, pp. 1549-1558, 1984; Pasquali, R., Cesari, M. P. Melchionda, N., Stefanini, C., Raitano, A. and Labo, G., *International Journal of Obesity*, vol. 11, pp. 163-168, 1987; Astrup, A., Lundsgaard, C., Madsen, J. and Christensen, N. J., *The American Journal of Clinical Nutrition*, vol. 42, pp. 83-94, 1985 and Astrup, A., Bulow, J., Madsen, J. and Christensen, N. J., *Journal of the American Physiological Society*, pp. E507-E515, 1985). The anorectic effect of ephedrine has also been investigated in rats (Zarrindast, M. R., Hosseini-Nia, T. and Farnoodi, F., *Gen. Pharmac.*, vol. 18, no. 5, pages 559-561, 1967). Ephedrine, used alone, results in increased thermogenesis, but also undesirable side effects in man, such as elevated blood pressure and tremors.

The thermogenic response to ephedrine in animals varies with the type of animal model studied. Dulloo and Miller (*British Journal of Nutrition*, loc. cit.) have studied the thermogenic properties of six sympathomimetic drugs in both mice and rats. The six drugs studied were ephedrine, methoxyphenamine, yohimbine, tranylcypromine, amitriptyline, iprindole and theophylline. The metabolic response of various mice and rat models differed with the respective drugs. For example, in mice made obese by chemical lesioning in the hypothalamus, all of the drugs with the exception of theophylline caused a reduction in body fat without loss of body protein. Similarly, all six drugs with the exception of theophylline resulted in a state of negative energy balance by means of a thermogenic effect. In contrast, in mice made obese by feeding a high protein, high fat diet, all seven drugs caused a negative energy imbalance. In genetically obese mice only ephedrine and tranylcypromine were found to have thermogenic activity. A similar variability in physiological effect was seen in the rat models.

The activity of thermogenic drugs in humans has been postulated to involve brown adipose tissue. However, this proposed mechanism of action has never been verified in humans.

Studies have also been reported investigating combinations of ephedrine with additional compounds such as caffeine. In 1972, a composition containing ephedrine, caffeine and phenobarbitol was noted as inducing loss of appetite and weight loss in humans. This composition, popularly known as the "Elsinore pill" was widely prescribed. However, serious side effects such as cutaneous reactions (tremors) were reported with this composition. Ephedrine/caffeine compositions without the presence of phenobarbitol were also been investigated in attempts to reduce the side effects of the Elsinore pill. However, patients receiving this "modified Elsinore pill" continue to suffer from tremors similar to the effects seen with the Elsinore pill (Malchow-Moller, A., Larsen, S., Hey, H., Stokholm, K. H., Juhl, E. and Quaade, F., *International Journal of Obesity*, vol. 5, pp. 183-187, 1981).

More recent studies of the thermogenic effects in humans of mixtures of ephedrine and methylxanthines, such as caffeine and theophylline, have been reported by Dulloo and Miller (*American Journal of Clinical Nutrition*, vol. 43, pp. 388-394, 1986 and *International Journal of Obesity*, vol. 10, pp. 467-481, 1986). These studies suggest that ephedrine/methylxanthine mixtures are more effective than ephedrine given alone. Methylxanthines are reported as potentiating the thermogenic anti-obesity effect of ephedrine leading to normalization of body weight and body composition. However, reports have also been published suggesting that caffeine has no potentiating effect on the action of ephedrine (Cesari, M. P., Pasquali, R., Casimirri, F., Melchionda, N., Stefanini, C. and Raitano, A., *Ist. Clin. Med. and Gastroenterol.*, Univ. Alma Mater, S. Orsola Hospital, Bologna, Italy).

Studies reporting the thermogenic effect of ephedrine/etilefrine (Pasquali, R., Cesari, M.P., Besteghi, L., Melchionda, N. and Balestra, V., *International Journal of Obesity*, vol. 11, Supplement 3, pp. 23-26, 1987) and ephedrine/aspirin (Dulloo, A. G. and Miller, D. S., *Am. J. Clin. Nutr.*, vol. 45, pp. 564-569, 1987) have also been reported. Results obtained with ephedrine/etilefrin were inconclusive. Aspirin appears to potentiate the thermogenic effects of ephedrine.

A need continues to exist for improved weight loss compositions which are safe, effective and exhibit reduced side effects in humans. Studies on the thermogenic and physiological effects of ephedrine and other compounds in rats and mice give varying results which cannot be directly applied to the use of these compounds in humans. The function of brown adipose tissues in humans is only speculative. The thermogenic effect demonstrated in animals has been postulated to proceed by means of brown adipose tissue in animals, an effect which cannot be directly applied to human treatment in view of the variable effects seen with sympathimometic drugs in animal studies. A new approach to weight loss composition and methods for use in humans is needed.

SUMMARY OF THE INVENTION

Accordingly, one object of the present invention is to provide a weight loss composition which produces significant weight loss. A further object is a weight loss composition which can be administered both in conjunction with caloric restriction (diet) and the absence of caloric restriction. A further object of the invention is to provide a weight loss composition and method producing weight loss which is effective in promoting additional weight loss in low energy adapted obese persons who have difficulty losing weight with conventional caloric restriction. Still a further object of the invention is to provide a method for maintaining weight loss which is achieved using commercial caloric restriction programs.

These and other objects which will become apparent from the following specification have been achieved by the present method for producing weight loss which comprises administering to a human a composition comprising an effective amount of each of aspirin, caffeine and ephedrine into pharmaceutical weight loss compositions containing an effective amount of these compounds.

BRIEF DESCRIPTION OF THE DRAWINGS

A more complete appreciation of the invention and many of the attendant advantages thereof will be readily obtained from the drawings, wherein.

DETAILED DESCRIPTION OF THE PREFERRED EMBODIMENTS

Figure 1:
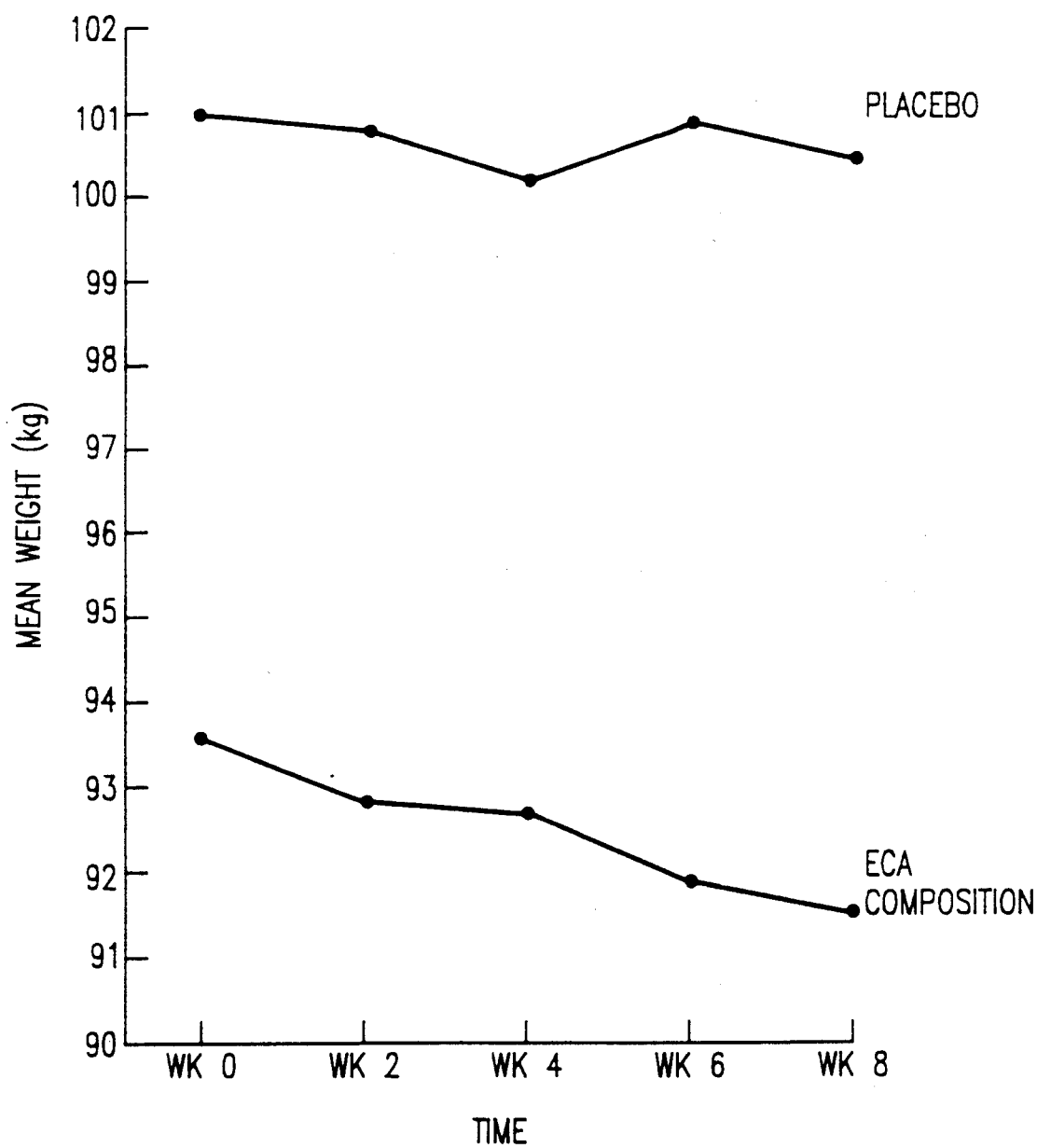
FIG. 1 shows the weight loss results for an eight-week treatment period comparing use of the composition of the present invention and a placebo.

The composition of the present invention is useful for producing weight loss in humans in a clinically obese condition. A person is "overweight", whose body weight (kg) is 15% above acceptable weight for that persons height (cm). Obesity has been defined using these measurements, as having a weight greater than 40% above acceptable weight (Dulloo, A.G. and Miller, D. S., *Wld Rev. Nutr. Diet.*, vol. 50, pp.1-56, 1987). However, the composition of the present invention is also useful for inducing weight loss in humans of relatively normal weight where additional weight loss is desirable. The composition can be formulated in any convenient pharmaceutical form and administered for the purpose of treating obesity, inducing weight loss, suppressing appetite, or maintaining weight control while on a diet or caloric restriction. In a particularly interesting application, the present composition can be used to induce weight loss in the person who has become low energy adapted following a regime of dieting. In such persons, initial weight loss due to caloric restriction is seen followed by a plateau phase in which additional weight loss is difficult as the dieting person's metabolic rate becomes low energy adapted. Administration of the present composition induces additional weight loss in such low energy adapted persons allowing additional weight loss.

Surprisingly, weight loss is effected using the present composition whether or not caloric restriction is employed concurrently. That is, there is no restriction with regard to caloric intake when using the present composition, and yet weight loss is induced. Obviously, when administered in conjunction with a commercial diet program, improved weight loss is observed and can be maintained.

In its broadest sense, the present invention is directed to a method for producing weight loss in a human by administering a composition containing a weight loss effective amount of aspirin, caffeine and ephedrine, all administered concurrently. In general, the amount of aspirin administered is about 30-2500 mg/day, preferably about 200-1000 mg/day. Caffeine is generally administered in amounts of about 10-500 mg/day, preferably about 30-200 mg/day. Ephedrine is administered in amounts of about 25-350 mg/day, preferably about 50-100 mg/day Most preferably, aspirin, caffeine and ephedrine are administered in amounts of about 300 mg/day, 120 mg/day and 150 mg/day, respectively. Obviously, amounts slightly above or below these general ranges may be used as long as a weight loss effective amount of each compound is present.

Each of aspirin, caffeine and ephedrine are commercially available. Aspirin (acetylsalicyclic acid) is well known and available as a white crystalline powder. Caffeine (1,3,7-trimethylxanthine) is also available as a white crystalline powder in both technical and pharmaceutical grades. Ephedrine possesses two assymetric carbon atoms and is therefore available in four different stereoisomers, that is, (−)-ephedrine, (+)-ephedrine, (−)-ψ-ephedrine and (+)-ψ-ephedrine, as well as two racemic mixtures. The stereoisomer (−)-ephedrine is much more effective and is therefore the preferred ephedrine stereoisomer for use in the present invention. However, the other stereoisomers of ephedrine are active in stimulating a thermogenic response and may be used in the present invention if desired. Ephedrine is also available as a white powder in technical and pharmaceutical grades.

In the method and composition of the present invention, the relative proportions of aspirin, caffeine and ephedrine are generally in the range of about 2.0:1.0:0.5 to about 3.5:1.0:2.0 for optimum effectiveness. Most preferably, aspirin, caffeine and ephedrine are present in relative amounts of about 2.75:1.0:1.25.

Administration of these general amounts of aspirin, caffeine and ephedrine, concurrently, produces onset of weight loss with substantially no increase in blood pressure, tremors or other side effects seen with conventional weight loss compositions and methods. Maintenance administration of the present composition allows one to maintain weight loss at the desired level after the initial amount of weight has been reduced. After weight loss, persons generally have more energy for daily activities and exhibit fewer undesirable side effects.

Surprisingly, the concurrent administration of aspirin, caffeine and ephedrine does not result in an increase in blood pressure. In contrast, other sympathomimetic drugs such as nicotine and propanolamine give rise to an increase in blood pressure. The present method results in larger increases in weight reduction with reduced side effects and lower dosages.

The composition of the invention is usually administered in the form of a pharmaceutical formulation or composition comprising the compounds of the invention together with a pharmaceutically acceptable carrier therefor.

The carrier must be "acceptable" in the sense of being compatible with the other ingredients of the formulation and not deleterious to the patient. Such carriers may be solid, liquid or gaseous materials suitable for the purpose of administering the medicament by the desired route.

These pharmaceutical compositions may be administered orally or parenterally (including subcutaneous, intramuscular and intraveneous injection) or as a suppository or pessary. In general the compositions are administered orally.

For parenteral administration the active compounds may be presented in sterile solutions or suspensions in aqueous or oleaginous vehicles, which may also contain preservatives and material for rendering the solution or suspension isotonic with the blood of the patient. The formulations are conveniently presented in unit-dose or multi-dose sealed containers.

For oral administration the pharmaceutical compositions may be formulated as a draught in water or in a syrup, in capsules, cachets, boluses or tablets, as an aqueous or oleaginous solution or suspension or in suspension in a syrup, such suspensions optionally including suspending agents, or as an oil-in-water or water-in-oil emulsion. Flavouring, sweetening, preserving, thickening or emulsifying agents may also be included in the formulation.

Tablets may contain the active compounds as a powder or granules optionally mixed with binders, lubricants, inert diluents or surface-active or dispersing agents and may be formed by compression or by molding in inert liquid diluent. Such tablets may be scored and/or coated.

Capsules and cachets may contain the active compounds alone as admixture or in a mixture with one or more other ingredients. Capsules may also contain the active compounds in aqueous or oleaginous solution suspension or emulsion optionally in association with other ingredients. For administration as a suppository or pessary the active compounds may be presented in admixture with a suitable carrier such as cocoa butter and other material commonly used in the art, and are conveniently shaped by molding. For administration in discrete unit dosage forms such as tablets, capsules, suppositories and pessaries as described above, the active compound is preferably present in the mg/day amounts discussed above, per tablet, capsule, suppository or pessary.

All the above formulations may be produced by standard processes comprising bringing the active compounds into association with one or more pharmaceutically acceptable carriers.

A unit dose of the composition of the present invention, preferably contains from 30-2500 mg aspirin, 10-500 mg caffeine and 25-350 mg ephedrine. More preferably, the unit dose comprises about 200-1000 mg aspirin, 30-200 mg caffeine and 50-100 mg ephedrine. A particularly preferred unit dose is about 300 mg aspirin, 120 mg caffeine and 150 mg ephedrine. Such unit dose compositions may be administered from 1 to 6 times per day such that the total daily dose is in the ranges mentioned above for the effective treatment.

The aspirin, caffeine and ephedrine used in the present invention may also be present as pharmaceutically acceptable salts if desired. Typical salts include hydrochloride, hydrobromide and maleate salts, although any pharmaceutically acceptable salt may be used.

Other features of the invention will become apparent in the course of the following descriptions of exemplary embodiments which are given for illustration of the invention and are not intended to be limiting thereof.

EXAMPLES

The safety and efficacy of a composition containing aspirin, caffeine and ephedrine (ECA) were studied in 24 obese human subjects. A total daily dosage of ephedrine (75 mg), caffeine (150 mg) and aspirin (300 mg) or a placebo was given in three pre-meal doses over an eight-week period in a double blind experiment. After four weeks, the ephedrine dose was increased to 150 mg/day. The subjects were not calorically restricted.

The overall weight loss with the composition was 2.2 kg versus 0.67 kg in subjects taking the placebo. When the initial and final weights were compared, significant differences were found in the test group taking the composition of the present invention at week 6 ($p<0.005$) and at week 8 ($p<0.001$), but not in the placebo group. Additionally, the rate of weight loss for the group of subjects taking the present composition was significantly greater than for the placebo ($p \leq 0.05$).

Neither the group taking the active composition nor the group taking the placebo showed significant changes in heart rate, blood pressure, serum glucose, insulin or cholesterol. There was no statistically significant difference in the frequency of reported side effects.

FIG. 1 shows the weight loss results for the eight-week treatment period in both the placebo group and the group taking the ECA composition. The untreated group weighed on the average about 8 kg more at the beginning of the study than the treated group. As can be seen from FIG. 1, the untreated group showed no trend toward weight loss, just random variation between about 100 and 101 kg over the course of the eight-week period. In contrast, the treatment group showed significant weight loss between week 0 and week 4 and a greater tendency toward weight loss after week 4 when the administered dose of ephedrine was doubled.

Figure 2:
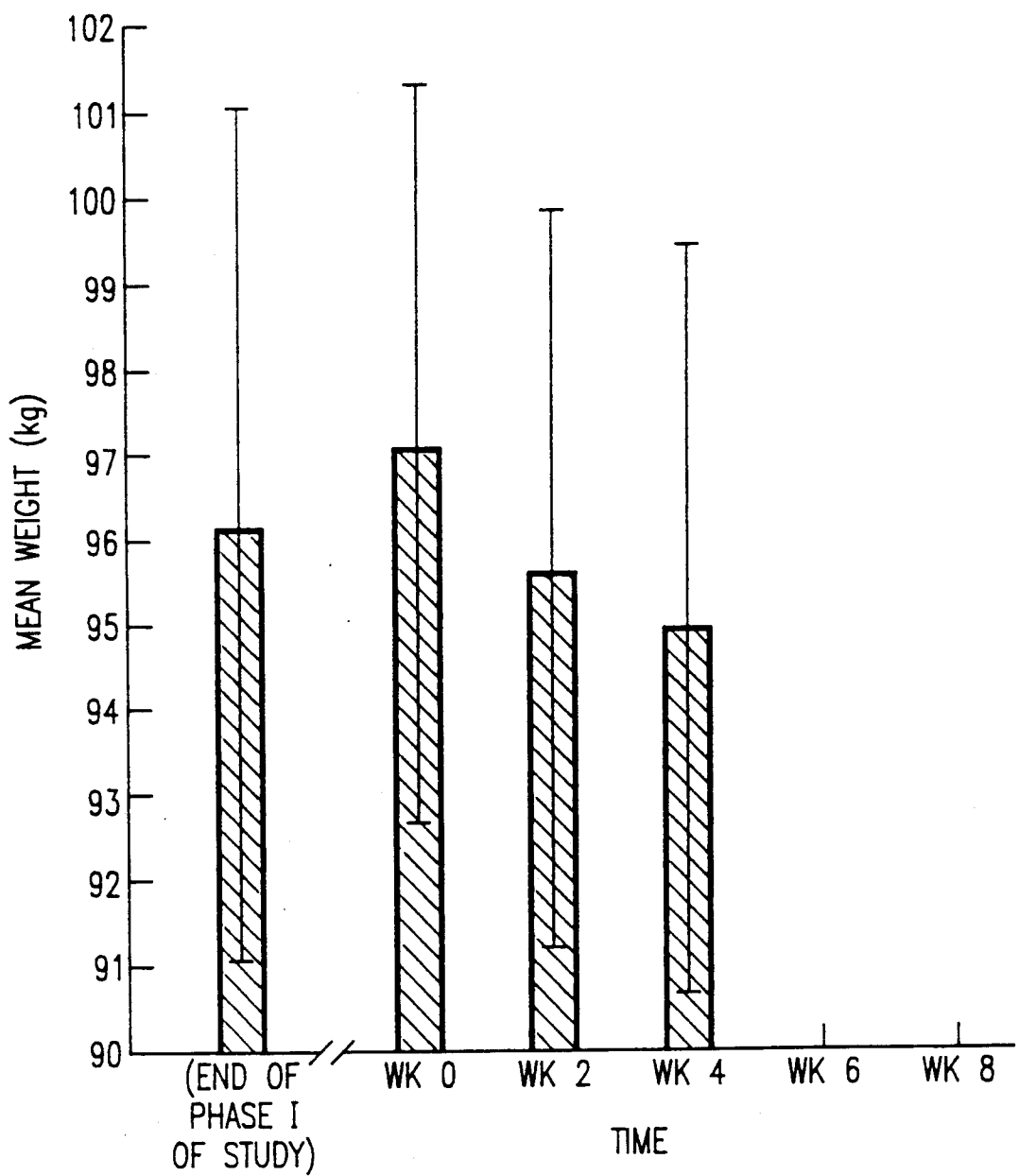
FIG. 2 shows a follow-up crossover study where the group receiving a placebo in the first phase of the study received the composition of the present invention in the crossover phase.

In a follow-up crossover study, the group of subjects receiving the placebo in the first phase of the study, now received the ECA composition (ephedrine—75 mg, caffeine 150 mg, aspirin—300 mg). At the beginning of the second phase study, the average weight of the subjects had increased by approximately 1 kg in the interval between the end of the first phase of the study and the beginning of the second phase as can be seen from FIG. 2. Over the four weeks of the second phase study, the average weight loss for participants in the second phase was approximately 2 kg. In contrast, this same group of subjects lost an average of only 0.6 kg during the entire eight-week period of the first phase study.

The crossover study clearly shows the efficacy of the ECA composition of the present invention for weight loss in humans, even without caloric restriction.

Obviously, numerous modifications and variations of the present invention are possible in light of the above teachings. Therefore, it is to be understood that the invention may be practiced other than as specifically described herein.

What is claimed as new and desired to be secured by Letters Patent of the United States is:

1. A method for producing weight loss in a human in need thereof, comprising administering thereto an effective amount of a composition comprising aspirin, caffeine and ephedrine or pharmaceutically acceptable salts thereof.

2. The method of claim 1, wherein about 30–2500 mg/day aspirin, about 10–500 mg/day caffeine and about 25–350 mg/day ephedrine are administered.

3. The method of claim 1, wherein about 200–1000 mg/day aspirin, about 30–200 mg/day caffeine and about 50–100 mg/day ephedrine are administered.

4. The method of claim 1, wherein about 300 mg/day aspirin, about 120 mg/day caffeine and about 150 mg/day ephedrine are administered.

5. The method of claim 1, wherein the amount of aspirin, caffeine and ephedrine administered is in a relative ratio of about 2.0:1.0:0.5 to about 3.5:1.0:2.0.

6. The method of claim 5, wherein said ratio is about 2.75:1.0:1.25.

7. The method of claim 1, wherein said composition is administered orally.

8. The method of claim 1, wherein said composition is in unit dose form.

9. The method of claim 8, wherein said unit dose comprises about 30–2500 mg aspirin, 10–500 mg caffeine and 25–350 mg ephedrine.

10. The method of claim 8, wherein said unit dose comprises about 200–1000 mg aspirin, 30–200 mg caffeine and 50–100 mg ephedrine.

11. The method of claim 8, wherein said unit dose comprises about 300 mg aspirin, 120 mg caffeine and 150 mg ephedrine.

12. The method of claim 1, wherein said composition is administered with a pharmaceutically acceptable carrier or excipient.

13. The method of claim 1, wherein said human is overweight or obese.

14. The method of claim 1, wherein said human is low energy adapted.

15. The method of clam 1, further comprising calorically restricting said human during said administering step.

16. A method for producing weight loss in a calorically restricted human in need thereof, comprising administering to the human a composition comprising an effective amount of each of aspirin, caffeine and ephedrine or pharmaceutically acceptable salts thereof.

17. The method of claim 16, wherein about 30–2500 mg/day aspirin, about 10–500 mg/day caffeine and about 25–350 mg/day ephedrine are administered.

18. The method of claim 16, wherein about 200–1000 mg/day aspirin, about 30–200 mg/day caffeine and about 50–100 mg/day ephedrine are administered.

19. The method of claim 16, wherein about 300 mg/day aspirin, about 120 mg/day caffeine and about 150 mg/day ephedrine are administered.

20. The method of claim 16, wherein the amount of aspirin, caffeine and ephedrine administered is in a relative ratio of about 2.0:1.0:0.5 to about 3.5:1.0:2.0.

21. The method of claim 16, wherein said ratio is about 2.75:1.0:1.25.

22. The method of claim 16, wherein said composition is administered orally.

23. The method of claim 16, wherein said composition is in unit dose form.

24. The method of claim 16, wherein said unit dose comprises about 30–2500 mg aspirin, 10–500 mg caffeine and 25–350 mg ephedrine.

25. The method of claim 16, wherein said unit dose comprises about 200–1000 mg aspirin, 30–200 mg caffeine and 50–100 mg ephedrine.

26. The method of claim 16, wherein said unit dose comprises about 300 mg aspirin, 120 mg caffeine and 150 mg ephedrine.

27. The method of claim 16, wherein said composition is administered with a pharmaceutically acceptable carrier or excipient.

28. The method of claim 16, wherein said human is low energy adapted.

* * * * *